United States Patent [19]

Frederiksen et al.

[11] Patent Number: 5,718,859
[45] Date of Patent: Feb. 17, 1998

[54] METHOD OF MOLDING A TAMPER-EVIDENT CLOSURE SEAL

[75] Inventors: Fred Frederiksen, Dallas; Oscar Salinas, Garland, both of Tex.

[73] Assignee: Sherwood Medical Company, St. Louis, Mo.

[21] Appl. No.: 818,025

[22] Filed: Mar. 14, 1997

Related U.S. Application Data

[60] Continuation of Ser. No. 459,680, Jun. 2, 1995, abandoned, which is a division of Ser. No. 178,953, Jan. 7, 1994, Pat. No. 5,506,015.

[51] Int. Cl.$^6$ ............... B28B 3/02; B29C 43/00; B31F 1/00
[52] U.S. Cl. .......... 264/152; 264/154; 264/155; 264/156; 264/296; 156/211
[58] Field of Search ............... 264/296, 155, 264/138, 152, 154, 156; 156/211, 230

[56] References Cited

U.S. PATENT DOCUMENTS

| | | | |
|---|---|---|---|
| 3,251,917 | 5/1966 | Burton et al. | 264/152 |
| 4,266,687 | 5/1981 | Cummings | 220/257 |
| 4,390,104 | 6/1983 | Cummings | 215/232 |
| 4,423,819 | 1/1984 | Cummings | 215/232 |
| 4,514,248 | 4/1985 | Cummings | 156/268 |
| 4,527,703 | 7/1985 | Cummings | 215/232 |
| 4,550,842 | 11/1985 | Cummings | 215/232 |
| 4,566,627 | 1/1986 | Gendron | 229/81 |
| 4,588,465 | 5/1986 | Paciorek | 156/220 |
| 4,678,083 | 7/1987 | Anderson | 206/459 |
| 4,917,867 | 4/1990 | Jensen et al. | 422/102 |
| 5,013,088 | 5/1991 | Marin | 283/81 |
| 5,319,475 | 6/1994 | Kay et al. | 359/2 |
| 5,324,380 | 6/1994 | Marin | 156/230 |

FOREIGN PATENT DOCUMENTS 2753239   6/1979   Germany.

*Primary Examiner*—Jan H. Silbaugh
*Assistant Examiner*—Robin S. Gray
*Attorney, Agent, or Firm*—Montgomery W. Smith; Grant D. Kang

[57] ABSTRACT

A tamper-evident closure seal for containers such as syringes or syringes with an attached needle. The seal includes a plurality of slits therein which inhibit removal of the seal from the container once the seal has been placed on the container. The method includes deformation of a portion of the slitted area of the seal in order to strengthen the seal in the area of the slits so as to improve removeability of the seal from its release liner prior to attachment thereof to the container, without inadvertent or premature destruction of the seal.

7 Claims, 3 Drawing Sheets

METHOD OF MOLDING A TAMPER-EVIDENT CLOSURE SEAL

This application is a continuation of application Ser. No. 08/459,680, filed Jun. 2, 1995, now abandoned, which is a division of Ser. No. 08/178,953, filed on Jan. 7, 1994, U.S. Pat. No. 5,506,015.

BACKGROUND OF THE INVENTION

1. Field of the Invention

This invention relates to tamper-evident closure seals for sealing of product containers, such as syringes and the like, and more specifically to the design of the seal which simplifies its removal from a release liner prior to its attachment to a container.

2. Description of Prior Art

It has been heretofore suggested to provide a tamper-evident seal to join a cap or other cover of a container to the container in such a way that subsequent removal of the cap or cover from the container is difficult or impossible without destroying the seal in a visually evident manner.

Tamper-resistive devices of this nature, however, are subject to a number of distinct deficiencies. First, since it is necessary to provide the seal with an extremely aggressive adhesive in order to best inhibit its removal from a container after it has been properly placed thereon, it is often difficult to manufacture the seal with a release liner that will adequately allow release of the seal therefrom for attachment to the container. Secondly, since it is also desirable that attempted removal of the seal from the container cause the seal to be destroyed in a visually evident manner so that any tampering with the previously sealed container becomes readily obvious to a later prospective user, slits are often provided in the seal which cause the seal to be torn apart into a plurality of pieces whenever removal thereof from the container is attempted.

Because of the desire to form a plurality of slits in the seal, and also to provide the seal with an extremely aggressive adhesive in order to improve the tamper resistive aspects of the seal, it has become increasingly difficult to provide a release liner of sufficiently low adhesion to allow removal of the seal therefrom in an intact state for placing the seal on the container. Often, a seal having a large number of slits and including an extremely aggressive adhesive is inadvertently destroyed prior to its use because of the inability to remove it intact from its release liner.

OBJECTS AND SUMMARY OF THE INVENTION

It is therefore, a primary object of the present invention to provide a novel and improved tamper-resistant closure seal which may be easily defeated for legitimate opening of the container, yet have a subsequent visual appearance which clearly evidences the fact that the container has been opened.

Another primary object of the present invention is to provide a tamper-resistant closure seal having an extremely aggressive adhesive which renders the seal extremely difficult to be removed from the container once attached.

Still another primary object of the present invention is to provide an improved tamper-resistant closure seal which includes a plurality of slits therein which substantially increase the likelihood that the seal will be destroyed if removal thereof from the container is attempted.

Yet another primary object of the present invention is to provide an improved tamper-resistant closure seal comprising a plurality of slits which have been modified in the manufacturing process of the seal to improve the releasability of the seal from its release liner without inadvertent destruction of the seal prior to its placement on a container.

These and other objects of the present invention are realized in a presently preferred embodiment of a tamper-resistant closure seal. The invention resides in the combination, construction, arrangement, disposition, and materials of the various component parts and elements incorporated in the improved tamper-resistant closure seal and in the methods of manufacture and use thereof. The present invention is better understood and objects and important features other than those specifically enumerated above will become better apparent when consideration is given to the following details and description, which when taken in conjunction with the attached drawings describes, discloses, illustrates and shows certain preferred embodiments or modifications of the present invention and what is presently considered and believed to be the best mode of practicing the principals thereof. Other embodiments or modifications of the present invention may be suggested to one having the benefit of the teachings herein, and such other embodiments or modifications are intended to be reserved and considered to fall within the scope and spirit of the present invention.

In accordance with the present invention, there is provided a tamper-evident closure seal for positioning around a container and a cap or cover therefor in an overlapping manner to provide a tamper-evident means for ensuring that removal or tampering with the cap or cover of the container will cause at least partial destruction of the seal in a manner which will be visually readily obvious to a later prospective user. The tamper-evident closure seal of the presently preferred embodiment preferably is of a laminated structure having a plurality of open slits formed therethrough in a predetermined pattern which covers substantially the entire surface of the seal. The bottom surface of the seal includes an aggressive adhesive to which is joined a release liner which covers the entire adhesive surface. The seal also includes a plurality of compressed areas, each of which intersect at least one slit and which cause the material adjacent the slit to be compressed together to close the slit and form a friction contact between the two side surfaces of the slit. This contact tends to temporarily strengthen the seal at the compressed area which had previously been weakened due to the formation of the slit. The compressed areas assist the seal in remaining intact while the release liner is removed therefrom prior to its attachment to a container. In addition to the advantages stated above, the seal of the present invention may also have its upper surface used as a coating area, such as for marking the type and quantity of material within the container. The coating may be accomplished by coloration of the seal, an inscription on the seal, the slit shape or slit pattern on the seal, or any combination thereof.

DETAILED DESCRIPTION OF THE INVENTION

Figure 1:
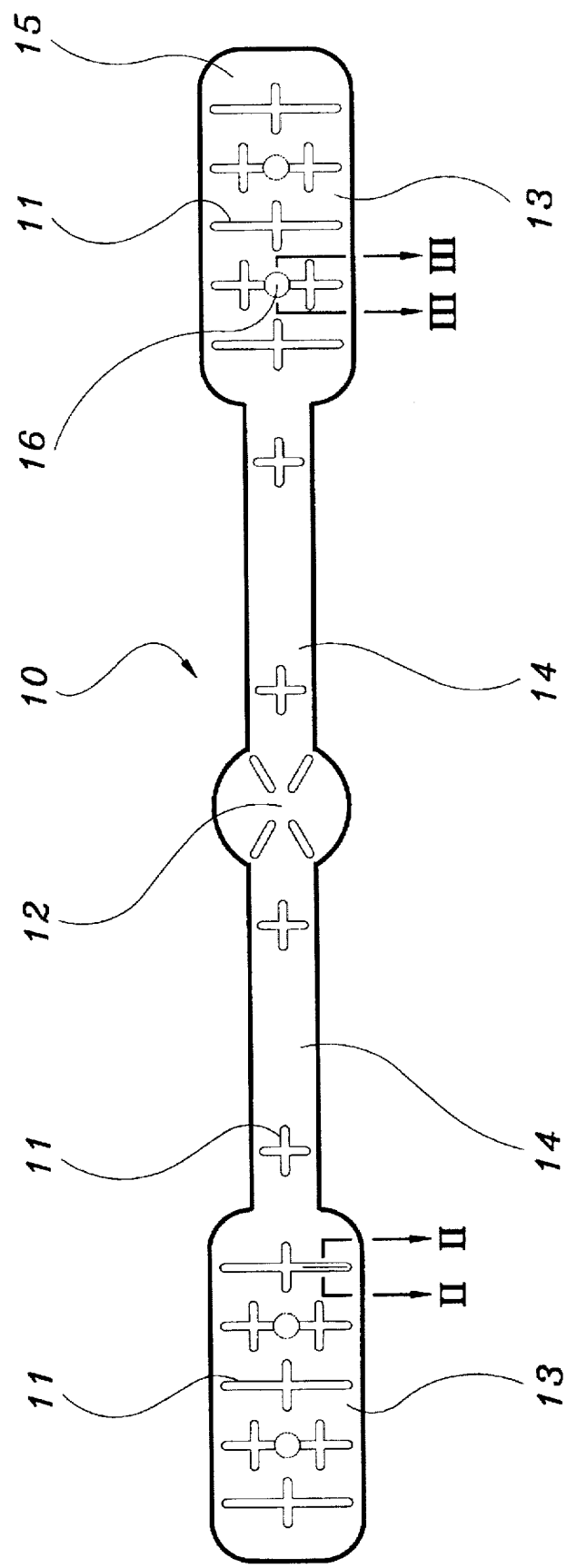
FIG. 1 is a plan view of a tamper-evident closure seal formed in accordance with the principles of the present invention.

As shown in the exemplary drawings, for purposes of illustration and not by means of limitation, an embodiment of a tamper-resistant closure seal made in accordance with the principles of the present invention is referred to generally by the reference numeral 10, and is provided for allowing visually readily obvious indication to a prospective user of tampering with the cap or closure of a container to which the seal has been attached.

More specifically, as shown in FIG. 1, seal 10 includes a plurality of slits 11 which have been formed in a preferred pattern over substantially the entire surface of the seal 10. The slits may be linear, curvilinear, or any other desired shape, and may be placed on the seal either horizontally, vertically, in criss-cross fashion, or in any other desired manner.

Further, if desired, the seal 10 can be shaped so as to include a central circular section 12 separated from two enlarged contact sections 13 by two diametrically opposed thin strip sections 14. Also, one or both of the enlarged contact sections 13 may include a tab 15 thereon for assistance in placing the seal 10 onto a container. The purpose of the particularly described shape of the preferred embodiment of the seal 10 will be explained below in conjunction with one of the preferred uses thereof.

The seal 10 is also formed with compressed areas 16 which traverse at least one slit 11 and have the function of strengthening the seal 10 at the slit area thereof to facilitate removal of the seal 10 from its release liner 17 as will be explained in more detail below.

Figure 2:
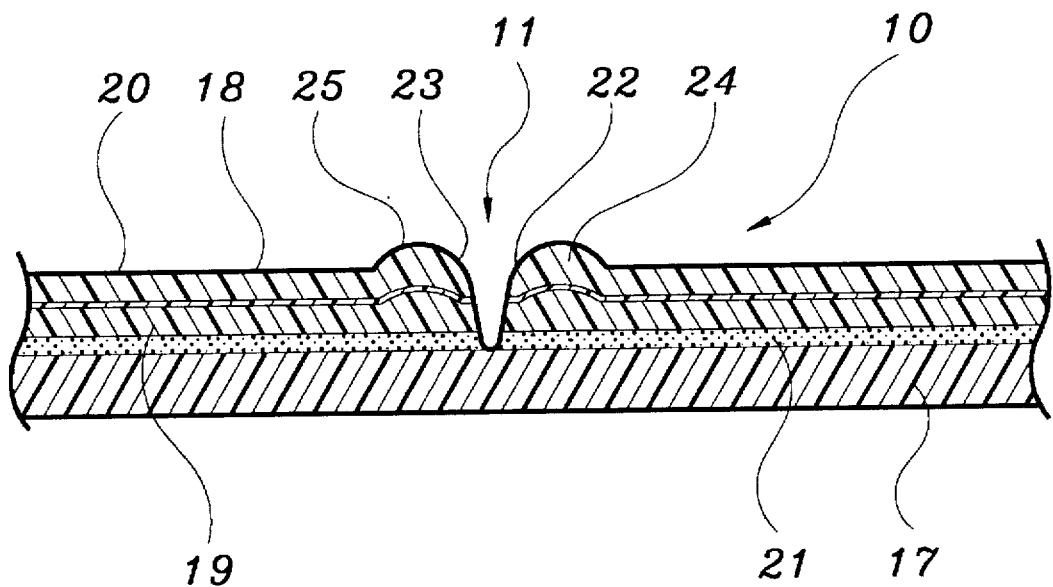
FIG. 2 is an enlarged cross-sectional view of the preferred embodiment of the seal of the present invention taken along line II—II of FIG. 1.

Referring now to FIG. 2, an enlarged cross-sectional view of the seal 10 of the present invention is shown. In the preferred embodiment of the present invention, the seal 10 is formed of a laminated structure including an upper layer 18 formed preferably of polypropylene. The upper layer 18 is joined to a bottom layer 19 by an adhesive intermediate layer 20. The bottom layer 19 is preferably formed of a litho-destructible material, but may be formed of other material such as vinyl or foil destructible materials. The bottom surface of the seal 10 is coated with an extremely aggressive adhesive 21 along the entire surface thereof, excluding the pull tab 15, however if desired. The entire bottom surface of the seal 10 is then covered by the release liner 17, which is preferably formed with a top surface having extremely low adhesion characteristics.

It should be noted that the seal 10 of the present invention is not limited to the particular materials or arrangement of materials forming the laminated structure as illustrated in the preferred embodiment of the present invention and as described above. Instead, the concept of the present invention may be implemented by the arrangement and selection of a number of materials and bonding systems which achieve the same overall effect of the improved seal 10, including the use of a single non-laminated material, if desired.

Referring further to FIG. 2, the slit 11 as shown therein forms two side surfaces 22 and 23 which are separated a distance approximately equal to the width of the instrument used to form the slit 11. Further, elevated areas 24 and 25 are formed directly adjacent the side surfaces 22 and 23 respectively due to displacement of seal material caused by the opening of the slit 11. The slit 11 may extend completely through the seal 10 but not through the release liner 17.

Figure 3:
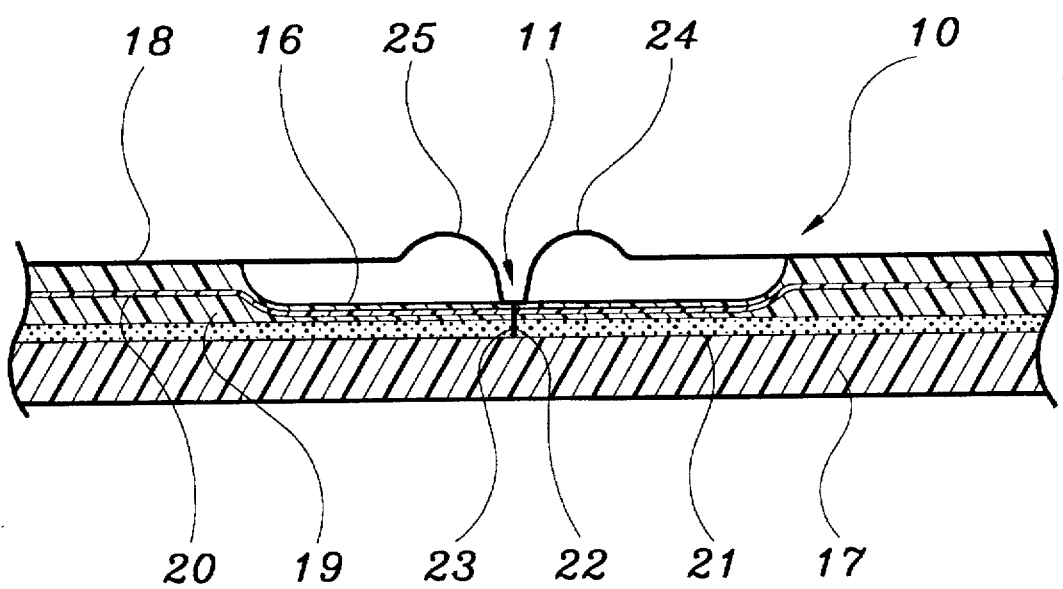
FIG. 3 is an enlarged cross-sectional view of the preferred embodiment of the seal of the present invention taken along line III—III of FIG. 1.

Referring now to FIG. 3, an enlarged cross-section through a compressed area 16 of the seal 10 is shown. The compressed area 16 is formed through the use of a tool (not shown) which is forced downwardly over at least one slit 11 in a predetermined position so as to deform the seal 10 and compress the side walls 22 and 23 of the slit 11 to a contacting position. In this manner, the slit 11, although still remaining in the seal 10, is nevertheless closed in the compressed areas 16. The seal 10 is subsequently strengthened in the compressed area 16 due to the frictional forces existing between the side surfaces 22 and 23.

Figure 4:
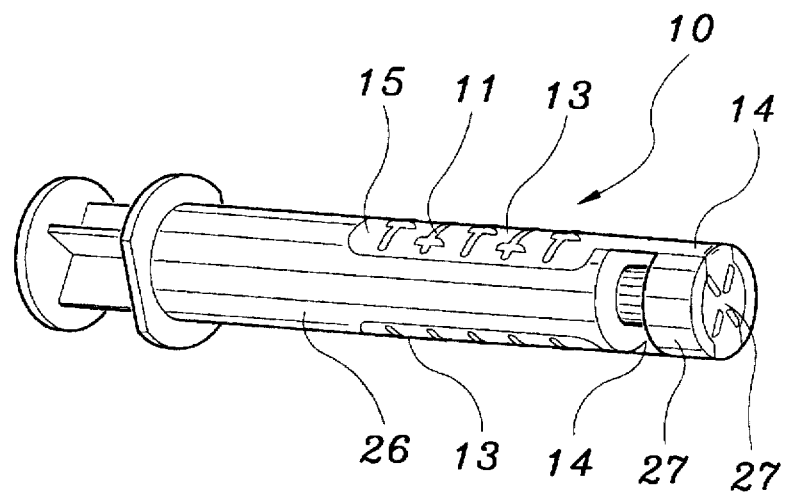
FIG. 4 is a perspective view of the preferred embodiment of the tamper-evident closure seal formed in accordance with the principals of the present invention showing a preferred method of attachment thereof to a container.

Referring now to FIG. 4, in use, the seal 10 of the present invention is removed from its release liner 17 and attached to a container and cap, such as the syringe 26 and cap 27, in the manner shown. When the seal 10 of the present invention is used specifically to cover the cap 27 of a syringe 26 which does not include a needle, the reason for the preferred shape of the seal 10 becomes readily evident. Specifically, the central circular section 12 of the seal 10 is positioned on top of the cap 27 with the enlarged contact sections 13 being positioned along the barrel of the syringe 26 housing, leaving the relatively thin strip sections 14 to span the area between the syringe barrel and the cap 27. In this manner, the thin strip sections 14 are the most likely areas of the seal 10 to be destroyed should removal of the cap 27 be attempted.

Figure 5:
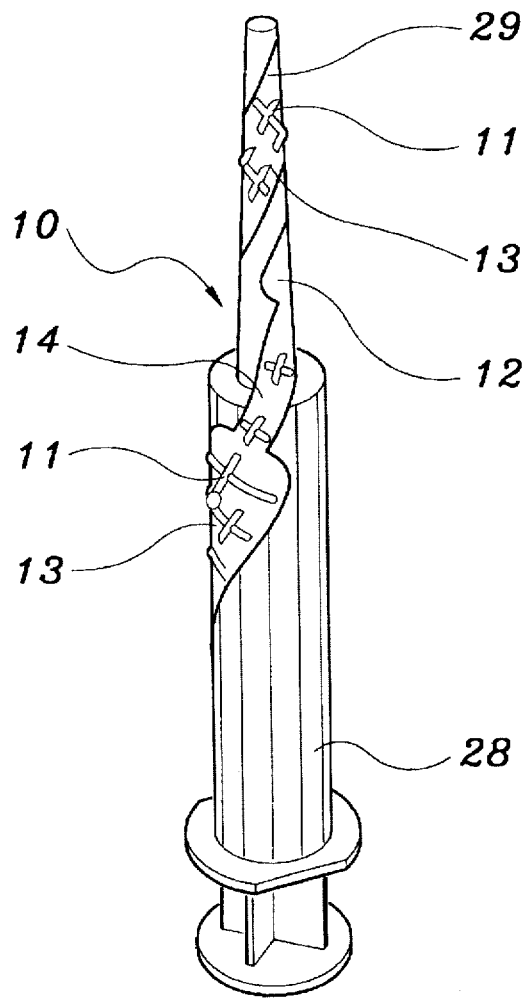
FIG. 5 is a front view of a preferred embodiment of the tamper-evident closure seal made in accordance with the principals of the present invention showing its attachment in a second preferred manner to a container.

The seal 10 of the present invention may however be used in several alternative ways. For example, FIG. 5 shows an alternative use of the seal 10 for sealing a syringe 28 having an elongate needle cover 29 thereon. As can be seen in the drawing, the seal 10 is attached so that one enlarged contact section 13 is positioned on the syringe 28 and the remainder of seal 10 is wrapped around the syringe 28 and needle cover 29 until the central circular section 12 and the opposing enlarged contact section 13 become attached to the needle cover 29. In this manner, one of the thin strip sections 14 spans the area between the needle cover 29 and the syringe 28 and thus is the most likely point in the seal 10 to be destroyed as a result of any attempted removal of the needle cover 29.

Should an attempt be made to remove the seal 10 by lifting the pull tab 15, the slits 11 positioned in the enlarged contact section 13 will cause the seal 10 to be destroyed by detachment of the pull tab 15 from the remainder of the seal 10, instead of allowing the enlarged contact section 13 to be pulled away from the syringe.

It will be apparent from the foregoing, that while particular embodiments of the present invention have been illustrated and described, various modifications can be made thereto without departing from the spirit and scope of the invention. Accordingly, it is not intended that the invention be limited except as by the appended claims.

We claim:

1. A method of forming a tamper-resistant seal including the steps of:

forming at least one open slit having side walls in a seal area of a tamper-resistant sealing material, compressing the tamper resistant sealing material by restricting said compressing to a compression area less than said seal area, said compression area including only a portion of said at least one open slit and a portion of the seal area adjacent said portion of said at least one open slit, such that said side walls corresponding to said portion of said at least one open slit are compressed together to a closed position, thereby forming said tamper-resistant seal.

2. The method of claim 1 wherein said step of forming said at least one open slit having side walls includes forming said side walls with opposing surfaces separated by a gap; and, wherein, said step of compressing a compression area such that said side walls corresponding to said portion of said at least one open slit are compressed together to a closed position includes compressing said opposing surfaces of said side walls corresponding to said portion of said at least one open slit into contact to thereby increase the strength of the seal across the at least one open slit due to frictional interference.

3. The method of claim 1 wherein the at least one open slit extends completely through the compression area.

4. A method of forming a tamper-resistant seal including the steps of:

forming a plurality of open slits having side walls in a seal area of a tamper-resistant sealing material, compressing the tamper resistant sealing material by restricting said compressing to a plurality of compression areas, each of said plurality of compression areas being less than said seal area, each of said plurality of compression areas including a portion of the seal area adjacent any one of said plurality of open slits such that said tamper-resistant sealing material is compressed to close only a portion of any one of said plurality of open slits and thereby form said tamper-resistant seal.

5. The method of forming a tamper-resistant seal according to claim 4 further comprising the step of:

forming a pattern from the plurality of open slits simultaneously with the step of forming said plurality of open slits in the sealing material.

6. The method of forming a tamper-resistant seal according to claim 4 and further comprising the step of:

forming a pattern from the plurality of compression areas simultaneously with the step of compressing said plurality of compression areas.

7. The method of claim 4 wherein the plurality of slits extend completely through the plurality of compression areas.

* * * * *